(12) United States Patent
Corson et al.

(10) Patent No.: US 7,627,435 B2
(45) Date of Patent: Dec. 1, 2009

(54) FILTERING OF PIXEL SIGNALS DURING ARRAY SCANNING

(75) Inventors: John F. Corson, Mountain View, CA (US); Kenneth L. Staton, San Carlos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 528 days.

(21) Appl. No.: 10/912,027

(22) Filed: Aug. 4, 2004

(65) Prior Publication Data

US 2006/0031028 A1 Feb. 9, 2006

(51) Int. Cl.
*G01N 33/48* (2006.01)
*G03D 3/04* (2006.01)
*G03B 7/00* (2006.01)
*G02B 5/32* (2006.01)
*G02B 26/10* (2006.01)
*G06K 9/46* (2006.01)
*G06K 9/66* (2006.01)
*G01N 21/86* (2006.01)

(52) U.S. Cl. .................. 702/19; 396/639; 396/223; 359/17; 382/194; 250/559.05

(58) Field of Classification Search .............. None
See application file for complete search history.

(56) References Cited

U.S. PATENT DOCUMENTS

| 4,686,655 A | * | 8/1987 | Hyatt .................. 367/59 |
| 2003/0165871 A1 | | 9/2003 | Corson et al. |
| 2003/0168579 A1 | | 9/2003 | Corson et al. |
| 2003/0203371 A1 | | 10/2003 | Corson et al. |
| 2004/0021911 A1 | | 2/2004 | Corson et al. |
| 2004/0023224 A1 | | 2/2004 | Corson et al. |
| 2004/0051790 A1 | * | 3/2004 | Tamaru et al. ........... 348/223.1 |
| 2004/0064264 A1 | | 4/2004 | Corson et al. |

OTHER PUBLICATIONS

Hamamoto et al., "A Computational Image Sensor with Adaptive Pixel-Based Integration Time," IEEE Journal of Solid-State Circuits, vol. 36 (2001) p. 580-585.*
Cheung et al. "Making and Reading Microarrays" Nature America Inc- Nature Genetics Supplement (1999) 21:15-18.

* cited by examiner

*Primary Examiner*—John S Brusca
*Assistant Examiner*—Anna Skibinsky

(57) ABSTRACT

Methods for evaluating a pixel signal produced during scanning of a chemical array are provided. In general, the subject methods involve identifying a set of conformant digital signals for a pixel, and integrating those signals. Also provided are systems and programming for performing the subject methods, and an array scanner containing these systems and programming.

15 Claims, 3 Drawing Sheets

FILTERING OF PIXEL SIGNALS DURING ARRAY SCANNING

BACKGROUND OF THE INVENTION

Arrays of surface-bound binding agents may be used to detect the presence of particular targets, e.g., biopolymers, in solution. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate, such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In certain instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many arraybased applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

For each pixel of a scan, a detector (e.g., a light detector such as a photomultiplier tube) typically detects light emitted from the surface of a microarray, and outputs an analog signal line that changes in amplitude according to the amount of emitted light entering the detector. This analog signal is usually sampled and digitized using an analog-to-digital converter (A/D converter) and integrated using a digital signal processor (DSP) to provide data, e.g., a numerical evaluation of the brightness of the pixel. This data is usually stored and analyzed at a later date.

During scanning, however, pixel signal "noise" (i.e., signals not related to the detected optical signal, for example electrical noise), may be present. This noise may be caused by other electronic circuitry, an electromagnetic disturbance, fluctuations in the intensity of the light used to excite the fluorescence, or a software or hardware error, for example. Pixel signals containing noise are typically digitized and integrated using similar methods to those for other signals, and, as such, inaccurate data may be produced from pixels signals containing signal noise.

Accordingly, there is a great need for methods for reducing the effects of signal noise on data production during scanning of a chemical array.

The present invention meets this, and other, needs.

Literature of interest includes: published U.S. Patent Applications: 20030168579, 20030165871, 20040064264, 20040023224, 20040021911, 20030203371 and 20030168579; and Cheung et al., Nature Genetics 1999, 21: 15-19.

SUMMARY OF THE INVENTION

Methods for evaluating a pixel signal produced during scanning of a chemical array are provided. In general, the subject methods involve identifying a set of conformant digital signals for a pixel, and integrating those signals. Using the subject methods, the non-conformant signals, i.e., the signals that correspond to undesirable signal noise, are generally filtered out prior to integration of the pixel signal. When the subject methods are employed, the resultant numerical evaluation is more accurate than if the methods are not employed. Also provided are systems and programming for performing the subject methods, and an array scanner containing these systems and programming.

In one embodiment, the invention provides a method of evaluating a signal for a pixel produced during scanning of a chemical array (e.g., a polypeptide or nucleic acid array). This method may involve providing a set of conformant digital signals for said pixel signal; and integrating the conformant digital signals, to evaluate the pixel signal.

In certain embodiments of the method, the conformant digital signals are produced by filtering signals in a time domain and in certain embodiments, the conformant digital signals are produced by filtering signals in a frequency domain. For example, the conformant digital signals are produced by: Fourier transforming the time samples of said pixel to produce a plurality of frequency components, reducing the magnitude of frequency components above a threshold as a function of their frequency, and reverse Fourier transforming the adjusted frequency components.

The method may produce data (i.e., a numerical evaluation) for a pixel, that may be output from a signal processor and, in certain embodiments, stored on a computer readable medium.

Other embodiments of the method may employ a filter to filter out any non-conformant digital signals prior to signal integration, or an algorithm to identify the conformant digital signals. These embodiments may involve: producing an analog signal for a pixel; digitizing the analog signal to provide a plurality of digital signals for said pixel; identifying a set of conformant digital signals from said plurality of digital signals; and integrating the conformant digital signals.

In another embodiment, the invention provides a chemical array scanner comprising a laser excitation system; a detection system that produces an signal representative of emitted light from the surface of an array; and a system for performing the above method. The scanner may contain an analog-to-digital converter; and a signal processor programmed to perform the above method. The scanner may contain a storage medium, e.g., computer memory, for storing data.

In another embodiment, the invention provides a computer-readable medium comprising: programming products for execution by a digital signal processor to produce data for a pixel, the programming comprising: instructions for identifying a set of conformant digital signals from a pixel signal; and instructions for integrating the conformant digital signals to produce data for the pixel. The computer-readable medium may further comprise instructions for executing the programming products when a pixel signal containing a non-conformant signal is detected. Also provided by the invention is a processor comprising the computer-readable medium and a chemical array scanner comprising the processor.

In a further embodiment, the invention provides a method of assaying a sample, comprising: (a) contacting said sample with a chemical array (e.g., a polypeptide or nucleic acid array) of two or more chemical ligands immobilized on a surface of a solid support; and (b) reading the array with a chemical array scanner according to the above to obtain data. This method may include: identifying a set of conformant digital signals from a plurality of digital signals for a pixel; and integrating the conformant digital signals to produce data for the pixel.

The invention also provides a kit for use in a chemical array optical scanner, containing: (a) a computer-readable medium according to the above; and (b) at least one chemical array.

DEFINITIONS

Figure 1:
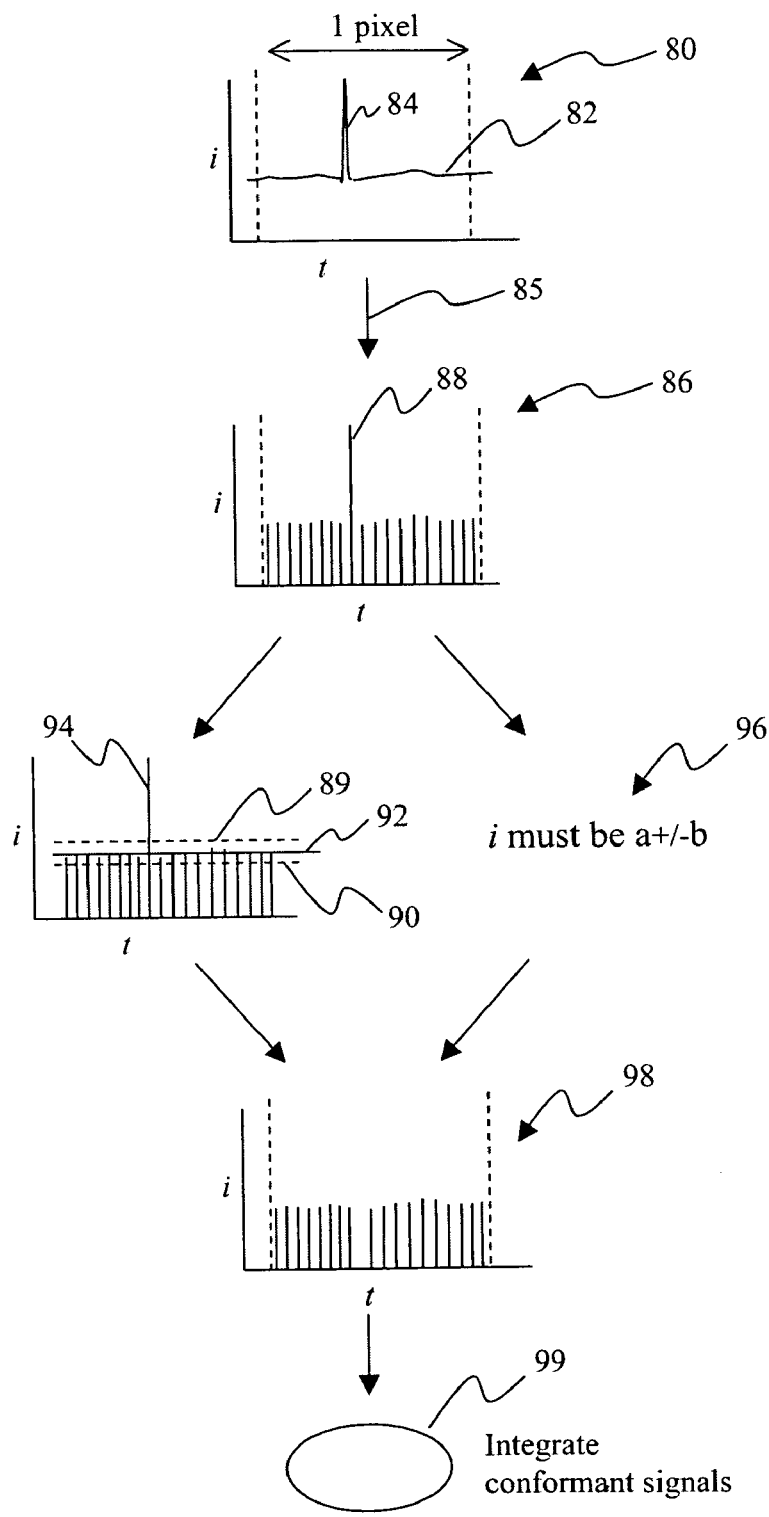
FIG. 1 schematically illustrates many general features of a first embodiment of the invention described herein.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), polypeptides (which term is used to include peptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," or "chemical array" includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In certain embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). If a device is "in communication with" another device, the devices are capable of transmitting or data or instructions to each other. Such devices may be networked to each other. "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "scanner" is device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either confocally (employing the same lens used to focus the light onto the array) or off-axis (using a separate lens positioned to one side of the lens used to focus the onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". Arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

The scanner typically used for the evaluation of arrays includes a scanning fluorometer. A number of different types of such devices are commercially available from different sources, such as such as Perkin-Elmer, Agilent, or Axon Instruments, etc., and examples of typical scanners are described in U.S. Pat. Nos. 5,091,652; 5,760,951, 6,320,196 and 6,355,934.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent. The term "evaluating a pixel" and grammatical equivalents thereof, are used to refer to measuring the strength, e.g., magnitude, of pixel signal to determine the brightness of a corresponding area present on the surface of an object scanned.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station. In certain embodiments, a processor may be a "signal processor", where a signal processor receives input signals and processes those signals. A signal processor may programmed or hard wired to perform one or more mathematical functions, such as those described below. In certain embodiments, a signal processor may "integrate" a set of digital signals (e.g., a set of digital signals representing an analog signal or a digitized version of an analog signal). By "integrating" is meant that a set of digital signals is input into a signal processor and the signal processor provides an output signal, in certain embodiments a single output signal, that represents the set of input signals. In many embodiments, the input set of digital signals may be integrated by summing the set of input signals, however, other means for integrating (e.g., averaging, etc.) are well known in the art. If an analog signal is referred to as being integrated, then it is understood that the analog signal is first digitized (i.e., sampled) prior to integration. For example, if an analog signal for a pixel is to be integrated, the signal is first sampled and digitized to provide a set of digital signals, and those digital signals are integrated by a signal processor to provide an output signal, typically a binary signal, that represents a numerical evaluation of the overall magnitude of the input set of digital signals (thereby providing a numerical evaluation of the magnitude of the analog signal for the pixel). The output of a signal processor may be referred herein as "data", and may be stored in memory.

As will be described in greater detail below, a digital signal may be a "conformant" or "non-conformant" signal based on whether the signal has a magnitude that is above or below a threshold magnitude. A "conformant" signal has a magnitude within a range defined by the threshold magnitude and a "non-conformant" signal has a magnitude outside of the range defined by the threshold magnitude. Non-conformant signals frequently result from system noise (e.g., electrical noise) not related to hybridization events (e.g., non-specific hybridization or the like). In other words, "non-conformant signals" are "outlier" signals that do not conform to a predetermined or normal signal range.

Data from reading an array may be raw data (such as fluorescence intensity readings for each feature in one or more color channels, or, for example, the output of a signal processor that has integrated a set of digital signals for a pixel) or may be processed data such as obtained by rejecting a reading for a feature which is below a predetermined threshold and/or forming conclusions based on the pattern read from the array (such as whether or not a particular target sequence may have been present in the sample). The data obtained from an array reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

The term "using" has its conventional meaning, and, as such, means employing, e.g. putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "providing" encompasses such terms as "generating", "identifying" and "producing".

DETAILED DESCRIPTION OF THE INVENTION

Methods for evaluating a pixel signal produced during scanning of a chemical array are provided. In general, the subject methods involve identifying a set of conformant digital signals for a pixel, and integrating those signals. Using the subject methods, the non-conformant signals, i.e., the signals that correspond to undesirable signal noise, are generally filtered out prior to integration of the pixel signal. When the subject methods are employed, the resultant numerical evaluation is more accurate than if the methods are not employed. Also provided are systems and programming for performing the subject methods, and an array scanner containing these systems and programming.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, system and methods aspects of the invention are first described. This discussion is followed by a description of suitable hardware for use in the invention.

The following U.S. patent applications are herein incorporated by reference in their entireties for all purposes: Ser. No. 10/912,661, entitled: "Methods and Compositions for Assessing Partially Saturated Pixel Signals", filed Aug. 4, 2004; Ser. No. 10/912,427, entitled: Multi-Gain Photodetection System for Array Analysis, filed Aug. 4, 2004; and Ser.

No. 10/912,463, entitled: "Detection of Feature Boundaries Pixels During Array Scanning", filed Aug. 4, 2004. The following published U.S. patent applications are incorporated by reference in their entirety, including all definitions, for all purposes: Ser. No. 10/086,932 (filed on Feb. 28, 2002 and published as 20030165871), Ser. No. 10/261,563 (filed on Sep. 30, 2002 and published as 20040064264), Ser. No. 10/212,191 (filed on Jul. 31, 2002 and published as 20040023224), Ser. No. 10/210,848 (filed on Jul. 31, 2002 and published as 20040021911), Ser. No. 10/137,658 (filed on Apr. 30, 2002 and published as 20030203371) and Ser. No. 10/086,658 (filed on Feb. 28, 2002 and published as 20030168579).

Methodology

As discussed briefly above, the invention provides a method for evaluating a pixel signal produced during scanning of a chemical array. In general, these methods involve providing (or, e.g., producing or identifying) a set of conformant signals for a pixel (i.e., a set of signals that have been filtered to remove outlier or noise signals), and integrating those conformant signals to provide an evaluation of the pixel. The conformant signals can be identified in a time domain (e.g., by excluding individual samples of a pixel signal) or in a frequency domain (e.g., by Fourier transforming a pixel signal and removing frequency components that are above a threshold frequency). In certain embodiments, therefore, the subject methods involve evaluating, usually by statistical methods, the plurality of digital signals to identify and exclude "outlier" signals that do not conform to a predetermined or normal signal range of the plurality of digital signals. In other embodiments, the subject methods may involve Fourier transforming signals to identify outlier signals by their frequency. Outlier signals typically are frequency components above a threshold frequency. These methods effectively act to "filter out" undesirable portions of a pixel signal prior to integration of the pixel signal.

Statistical methodologies for use in the subject methods are generally well known in the art, and need not be described in any great detail. For example, for a plurality of pixel signals for a pixel that is not a feature boundary pixel signal (and therefore having an approximately flat signal line), the methods may involve calculating a mean (i.e., average) signal intensity for the plurality of pixel signals, and a standard deviation of signal intensity for the signals. Signals that do not conform to the normal signal range of the plurality of digital signals may be identified by determining which signals have intensities that are greater than a certain number of standard deviations, e.g., 2, 3, 4, 5, 6, 7, 8 or more, usually up to about 10 or 20 or more standard deviations, away from the mean intensity. Alternatively, in other embodiments, the subject methods may characterize the intensities of the pixel signals by calculating a line of best fit (that may include error bars) by regression, and by calculating which of the pixel signals do not conform to (i.e., are not described by) the line. Such methods are standard in the statistical arts. Once identified, the "outlier" signals for a pixel may be excluded or ignored when integrating the plurality of digital signals. Such methods are generally referred to as filtering in a "time" domain.

Without wishing to limit the invention in any way, an exemplary method of filtering in a time domain is schematically set forth in FIG. 1.

Graph 80 of FIG. 1 shows an analog signal line 82 for a pixel, plotted as intensity i versus intensity t in which a portion of the signal line is non-conformant 84. In many embodiments, the signal is sampled and digitized 85, to provide a plurality of digital signals for the pixel, shown in graph 86. The non-conformant portion of the analog signal line is represented by digital signal 88. In one exemplary embodiment of this method, the plurality of digital signals for the pixel are evaluated by providing a line of best fit for the signal intensities 92, including an evaluation of the range of acceptable signal intensity variation 89 and 90. The non-conformant digital signal is identified because its intensity falls outside of this range, and may be ignored to provide a set of conformant digital signals for a pixel, diagrammatically illustrated in graph 98, which are integrated 99. In another exemplary embodiment of this method, the signals intensities are averaged, and a range of acceptable signal intensity variation is provided 96, e.g., as a multiple of a standard deviation/error of the signal intensities relative to the average. Such analysis may indicate that acceptable signal intensity variation i should be within certain limits, in this case a (e.g., the average signal intensity)+/−b (e.g., a multiple of a standard deviation/error of the signal intensities). The non-conformant digital signal is identified because its intensity falls outside of this range, and may be ignored to provide a set of conformant digital signals for a pixel, diagrammatically illustrated in graph 98, which are integrated 99 to provide an evaluation of the pixel.

Signals may also be filtered in a "frequency" domain. In one embodiment, these methods involve Fourier transforming a signal (over a period of time) to provide the relative strength and phase of frequency components of the signal, and filtering out undesirable frequencies. The maximum frequency component is related to the inverse of the minimum time between samples, and the minimum frequency component is related to the inverse of the entire length of time that is taken to acquire an entire pixel. In general, filtering using frequency domain methods generally involves Fourier transforming a signal, removing frequency components that are higher than a selected threshold frequency, and reverse Fourier transforming the data (minus the omitted frequency components). The threshold frequency may be related to the maximum rate at which the signal for a pixel can change assuming that the excitation source is constant, focused to a certain size and moving at a certain speed across an array.

In one embodiment described solely to exemplify signal filtering in a frequency domain, a focused laser spot of 5 microns (full width half max), w, is moving across an array at a speed of 1 meter/second, v. This laser passes across a perfectly sharp edge from a surface area void of fluorescent molecules to a surface area containing a significant amount of fluorescent molecules. In this embodiment, the signal increases at a frequency that is generally related to the inverse of the amount of time that it takes the entire beam (or at least half of it) to cross this perfectly sharp threshold. In this case, the frequency would be the inverse of v/w (which is generally correct to within factors of order unity that are determined by the shape of the beam). In this example, it would be frequencies above the order w/v that would be excluded from the signal.

The threshold frequency could be either theoretically calculated or measured experimentally for the instrument in question. For example, the threshold frequency could be evaluated by scanning a sample with a sharp non-fluorescent to fluorescent transition to provide a dim to bright signal (over time, relative to the dynamic range of the scanner) that is sharp relative to the size of the spatial resolution of the scanner. If several samples are evaluated using these methods, then the frequency response of the system can be determined. The frequency response of noise can also be measured in different signal intensity ranges. Using these measurements a frequency limit (or a limit for different signal intensity ranges) can be chosen that removes noise, or outlier signals, preferentially over signal in an optimal manner for that system and that signal range.

Figure 2:
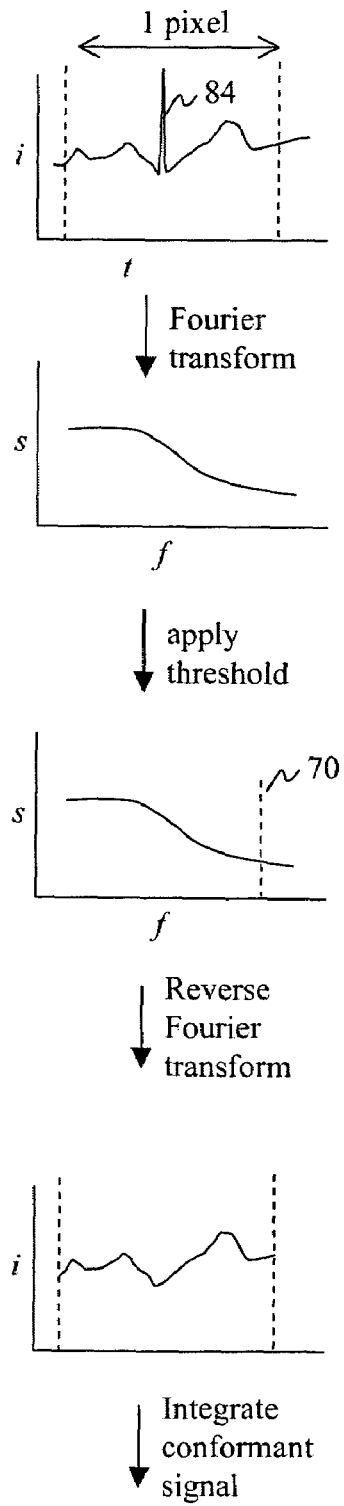
FIG. 2 schematically illustrates many general features of a second embodiment of the invention described herein.

An exemplary method for filtering a signal using in a frequency domain is shown in FIG. 2. In this embodiment, a pixel signal containing noise 84 is Fourier transformed, and the signal s plotted against frequency f. A threshold frequency 70 (which may be arbitrarily or experimentally determined, for example) is applied to identify frequencies that are below the threshold, and those frequencies below the threshold are reverse Fourier transformed to produce a conformant signal (i.e., a signal with reduced noise). This conformant signal may be integrated to produce data (e.g., such as a numerical evaluation) relating to the pixel.

In certain embodiments, the magnitudes of frequency components having frequencies above a threshold frequency may be reduced as a function of their frequencies. In other words, if a signal contains several frequency components that are above a threshold frequency, the magnitude of those frequency components may each be reduced by an amount that depends on its frequency. In general, the higher the frequency, the greater the reduction in magnitude. Accordingly, if the magnitude of several frequency components are reduced, the magnitude of the higher frequency components are reduced to a greater extent than the magnitude of the lower frequency components. Accordingly, in certain embodiments, the methods may provide a sliding scale of reductions to the magnitudes of a plurality of frequency components. The magnitudes may be reduced by any percentage at or between about 10% and about 100%, for example. In an exemplary embodiments, the magnitude of a frequency may be reduced by about 100% (i.e., reduced to zero), up to about 80%, up to about 50%, up to about 30% or up to about 20%, for example. As would be apparent to one of skill in the art, the amount by which a magnitude of a frequency component may be reduced may be determined by a series of pre-determined threshold frequencies. As discussed above, such threshold frequencies could be experimentally determined.

Both of the filtering methods described above are particularly useful in a system that is not photon-shot noise limited. Further, both of the filtering methods described above are most useful when the total number of integrated photons detected during a pixel is large compared to the total number of samples in the pixel (e.g., by a factor of about 2 or more, about 5 or more or about 10 or more).

In certain embodiments, the subject methods may be done in "real-time". In other words, the single integrated signal or data for a pixel obtained using the subject methods is generally output from the processor prior to processing of the signals for the next pixel. In particular embodiments for example, data obtained from a signal may be stored in a buffer and analyzed while accumulating data from a future pixel, e.g., the next pixel scanned.

Computer-Related Embodiments

The invention also provides a variety of computer-related embodiments. Specifically, the methods described above may be executed by using a computer program product comprising programming for execution by a digital system processor. Accordingly, the invention provides a digital signal processor programmed to identify a set of conformant digital signals from a plurality of digital signals for a pixel, and integrate those conformant digital signals to produce data for a pixel. The programming may be coded onto computer-readable medium, and the programming and the processor may be part of a computer-based system.

In certain embodiments, the above methods are coded onto a computer-readable medium in the form of "programming" or "programming products", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Optical Scanners

The subject systems and methods find particular use in chemical, e.g., biopolymeric, array scanners. Accordingly, also provided by the subject invention is a chemical array scanner that contains a system for performing the subject methods described above. Typically, such scanners have a laser excitation system for emitting light from the surface of a chemical array, hardware for performing the methods described above, and, usually, a storage medium for storing data produced by scanning. A subject scanner may also contain programming for executing the subject methods.

Any array scanner or device may be provided to include the above programming. Representative optical scanners of interest include those described in U.S. Pat. Nos. 5,585,639; 5,760,951; 5,763,870; 6,084,991; 6,222,664; 6,284,465; 6,329,196; 6,371,370 and 6,406,849—the disclosures of which are herein incorporated by reference. An exemplary optical scanner as may be used in the present invention is shown in FIG. 3.

Figure 3:
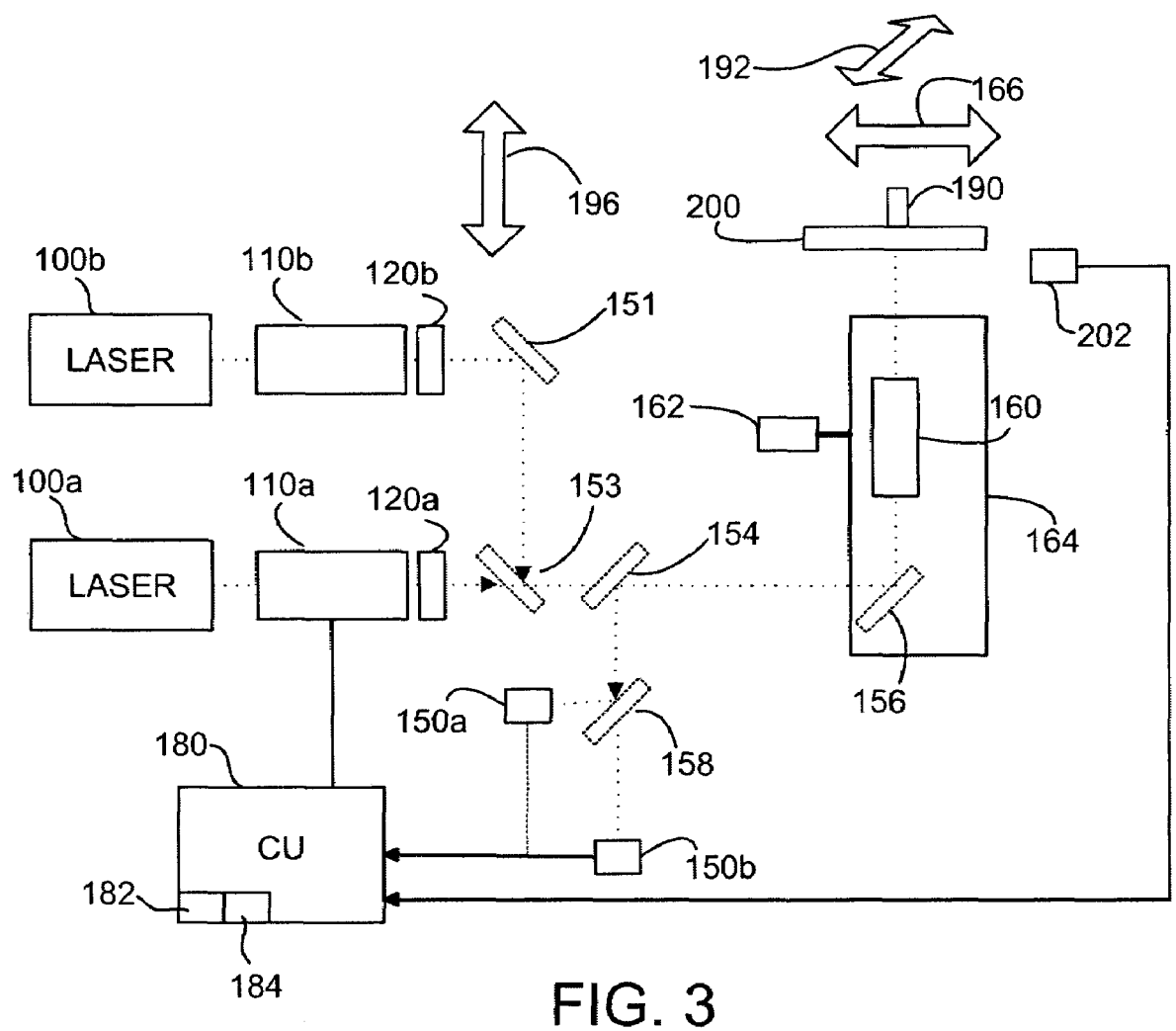
FIG. 3 schematically illustrates an apparatus as may be used in the present invention.

Referring now to FIG. 3, an exemplary apparatus of the present invention (which may be generally referenced as an "array scanner") is illustrated. A light system provides light from a laser 100 which passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100a, 100b is transmitted through a dichroic beam splitter 154, reflected off fully reflecting mirror 156 and focused onto an array mounted on holder 200, using optical components in beam focuser 160. Light emitted (in particular, fluorescence) at two different wavelengths (e.g., green and red light) from features on the array, in response to the interrogating light, is imaged using the same optics in focuser/scanner 160, and is reflected off mirrors 156 and 154. The two different wavelengths are separated by a further dichroic mirror 158 and are passed to respective detectors 150a and 150b. Depending on how the subject methods are implemented, a subject scanner may contain more than one of 150a, and more than one of 150b, or, in alternate embodiments, 150a and 150b may be multi-gain detectors.

More optical components (not shown) may be used between the dichroic and each detector 150a, 150b (such as lenses, pinholes, filters, fibers, etc.) and each detector 150a, 150b may be of various different types (e.g., a photo-multiplier tube (PMT), or photodiode or avalanche photodiode device (APD), such as a charge-coupled device (CCD), a charge-injection device (CID), or a complementary-metal-oxide-semiconductor detector (CMOS) device). All of the optical components through which light emitted from an array or calibration member 230 in response to the illuminating laser light, passes to detectors 150a, 150b, together with those detectors, form a detection system. This detection system has a fixed focal plane. A scan system causes the illuminating region in the form of a light spot from each laser 100a, 100b, and a detecting region of each detector 150a, 150b (which detecting region will form a pixel in the detected image), to be scanned across multiple regions of an array or array package mounted on holder 200. The scanned regions for an array will include at least the multiple features of the array. In particular the scanning system is typically a line by line scanner, scanning the interrogating light in a line across an array when at the reading position, in a direction of arrow 166, then moving ("transitioning") the interrogating light in a direction into/out of the paper as viewed in FIG. 3 to a position at an end of a next line, and repeating the line scanning and transitioning until the entire array has been scanned. In certain embodiments, a subject apparatus may scan a line multiple times before making a perpendicular transition.

This scanning feature is accomplished by providing a housing 164 containing mirror 158 and focuser 160, which housing 164 can be moved along a line of pixels (i.e., from left to right or the reverse as viewed in FIG. 3) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 3 may further include a reader (not shown) which reads an identifier from an array package. When identifier 40 is in the form of a bar code, that reader may be a suitable bar code reader.

Of course, the movements 166 and 192 may be accomplished by actuating holder 200 or housing 164 alone. Still further, the movement roles described for each element above may be swapped.

The system may also include detector 202, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, autofocus system 202 may contain a position detector e.g. a quadrature position encoder, also feeding back to the CU measures the absolute position (i.e., relative to the apparatus) of the servo-controlled adjuster 190. As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors.

Controller 180 of the apparatus is connected to receive signals from detectors 150a, 150b (these different signals being different "channels"), namely a signal which results at each of the multiple detected wavelengths from emitted light for each scanned region of array 12 when at the reading position mounted in holder 200. Controller 180 also receives the signal from autofocus detector 202, and provides the control signal to EOM 110, and controls the scan system. Controller 180 contains all the necessary software to detect signals from detector 202, and regulate a motorized or servo-controlled adjuster 190 through a control loop. Controller 180 may also analyze, store, and/or output data relating to emitted signals received from detectors 150a, 150b in a known manner.

Controller 180 also includes a digital signal processor for performing the methods described above. In certain embodiments, controller 180 includes a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

In one mode of operation, an array in a package is typically first exposed to a liquid sample. This liquid sample may be placed directly on the array or introduced into a chamber through a septa in the housing of the array. After a time to allow, for example, hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

The saved results from a sample exposed array, read with the methods described above, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

While it is noted that a scanner that reverses scanning direction at the end of each scan line (i.e. a bi-directional scanner) is disclosed, unidirectional scanners also find use with the methods of the invention.

Utility

The subject array scanners find use in a variety applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array.

In reading the array, pixel signals are usually processed using the methods described above.

It is further noted that aspects of the invention may be applicable to a variety of optical scanners including those that detect chemiluminescent or electroluminescent labels. The present invention will be applicable to such scanners where powering down the scanner will result in lifetime savings, as exemplified above.

Certain embodiments of the invention may involve transmitting data obtained from a method described above from a first location to a remote location. Certain other embodiments of the invention may involve receiving, from a remote location, data obtained from a method described above.

Kits

Kits for use in connection with the subject invention may also be provided. Such kits usually include at least a computer readable medium including computer programming products as discussed above and, in certain kits, instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In addition to the subject programming and instructions, the kits may also include one or more reference arrays, e.g., two or more reference arrays for use in testing an optical scanner after software installation.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of evaluating a signal produced during scanning of a chemical array by a chemical array scanner for generating an integrated single pixel signal, comprising:
   identifying a set of conformant digital signals and a set of non-conformant digital signals for generating said single pixel signal, wherein said conformant digital signals have a magnitude within a range defined by a threshold and said non-conformant digital signals have a magnitude outside of said range; then
   integrating said conformant digital signals and not the non-conformant digital signals, wherein said integrating produces data for generating said single pixel; and
   storing said data on a computer hard-drive, wherein said data is produced by said scanner and said method is implemented by said scanner.

2. The method of claim 1, wherein said array is a nucleic acid array.

3. The method of claim 1, wherein said array is a polypeptide array.

4. The method of claim 1, wherein said conformant digital signals are produced by filtering signals in a time domain.

5. The method of claim 1, wherein said conformant digital signals are produced by filtering signals in a frequency domain.

6. The method of claim 5, wherein said conformant digital signals are produced by:
   a) Fourier transforming time samples of said pixel to produce a plurality of frequency components,
   b) reducing the magnitude of frequency components above a threshold as a function of their frequency, and
   c) reverse Fourier transforming the adjusted frequency components.

7. The method of claim 1, wherein said data is output from a digital signal processor.

8. The method of claim 1, wherein the method comprises filtering out any non-conformant digital signals prior to signal integration.

9. The method of claim 1, wherein said method employs an algorithm to identify said conformant digital signals.

10. The method of claim 1, wherein said method comprises:
    producing an analog signal for said pixel;
    digitizing said analog signal to provide a plurality of digital signals for said pixel;
    identifying a set of conformant digital signals from said plurality of digital signals; and
    integrating said conformant digital signals.

11. A computer-readable storage medium comprising:
    programming products for execution by a digital signal processor, wherein said programming products produce data for a pixel when executed by said digital signal processor, said programming products comprising:
    instructions for performing the method of claim 1.

12. The computer-readable storage medium of claim 11, wherein said computer-readable storage medium further comprises instructions for executing said programming products when a pixel signal containing a non-conformant signal is detected.

13. A processor comprising the computer-readable storage medium of claim 11.

14. A chemical array scanner comprising the processor of claim 13.

15. A kit for use in a chemical array optical scanner, said kit comprising:
    (a) a computer-readable storage medium according to claim 11; and
    (b) at least one chemical array.

* * * * *